United States Patent [19]

Alker et al.

[11] Patent Number: 5,418,229
[45] Date of Patent: May 23, 1995

[54] MUSCARINIC RECEPTOR ANTAGONISTS

[76] Inventors: David Alker; Peter E. Cross, both of c/o Pfizer Central Research, Sandwich, England

[21] Appl. No.: 251,037

[22] Filed: May 31, 1994

Related U.S. Application Data

[63] Continuation of Ser. No. 877,166, filed as PCT/EP90/02044, Nov. 28, 1990.

[30] Foreign Application Priority Data

Jan. 6, 1990 [GB] United Kingdom ............... 9000302

[51] Int. Cl.$^6$ .............. A61K 31/55; C07D 243/38; C07D 471/04
[52] U.S. Cl. ................... 514/220; 540/495
[58] Field of Search .................. 540/495; 514/220

[56] References Cited

U.S. PATENT DOCUMENTS

| | | | |
|---|---|---|---|
| 4,210,648 | 7/1980 | Schmidt et al. | 540/495 |
| 5,002,943 | 3/1991 | Mihm et al. | 514/220 |
| 5,026,699 | 6/1991 | Mihm et al. | 514/220 |

*Primary Examiner*—Mukund J. Shah
*Assistant Examiner*—Philip I. Datlow
*Attorney, Agent, or Firm*—Peter C. Richardson; Cezina Holtrust; B. Timothy Creagan

[57] ABSTRACT

A compound of the formula

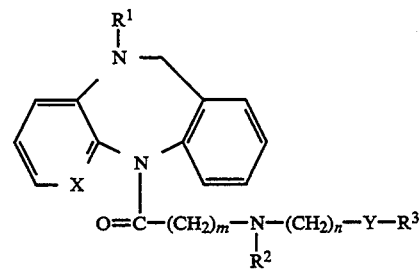

wherein X, $R^1$, $R^2$, $R^3$, $R^4$, Y, m and n are defined herein are useful as muscarinic receptor antagonists.

6 Claims, No Drawings

MUSCARINIC RECEPTOR ANTAGONISTS

This is a continuation, of application Ser. No. 07/877,166, filed as PCT/EP90/02044, Nov. 28, 1990, now abandoned.

BACKGROUND OF THE INVENTION

This invention relates to certain benzodiazepinone derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, divertitular disease, urinary incontinence, oesophageal achalasia and chronic obstructive airways disease.

SUMMARY OF THE INVENTION

According to the invention there are provided compounds of the formula:

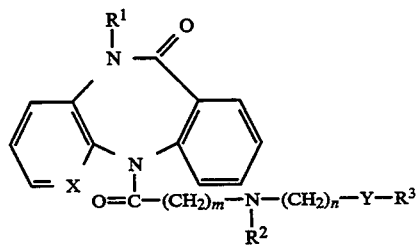
(I)

and their pharmaceutically acceptable salts, wherein X is N or

where
$R^4$ is H, halo or $C_1$-$C_4$ alkyl;
$R^1$ is H or $C_1$-$C_4$ alkyl;
$R^2$ is H or $C_1$-$C_4$ alkyl;
Y is a direct link, O or S;
m is an integer of from 1 to 4;
n is 2 or 3; and
$R^3$ is 1- or 2-naphthyl or a group of the formula:

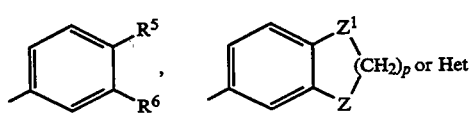

where
$R^5$ and $R^6$ are each independently H, $C_1$-$C_4$ alkyl, $C_1$-$C_4$ alkoxy, —$(CH_2)_q$OH, halo, trifluoromethyl cyano, —$(CH_2)_q NR^7 R^8$, —$OCO(C_1$-$C_4$ alkyl) —$SO_2 NH_2$ or —$CONR^9 R^{10}$, where either $R^7$ and $R^8$ are each independently H or $C_1$-$C_4$ alkyl, or
$R^7$ is H and $R^8$ is —$SO_2(C_1$-$C_4$ alkyl), —$CONR^9 R^{10}$, —$CO(C_1$-$C_4$ alkyl) or —$SO_2 NH_2$;
$R^9$ and $R^{10}$ are each independently H or $C_1$-$C_4$ alkyl;
q is 0, 1 or 2;
Z and $Z^1$ are each independently O or $CH_2$;
p is 1, 2 or 3; and "Het" is pyridyl, pyrazinyl or thienyl.

Preferably, $R^1$ is H. X is preferably N or CH. m is preferably 1, 2 or 3. n is preferably 2. $R^2$ is preferably methyl. Y is preferably a direct link or O.

$R^3$ is preferably 2-naphthyl, pyridyl or a group of the formula:

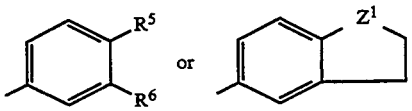

where $R^5$ and $R^6$ are each independently H, $C_1$-$C_4$ alkyl, $C_1$-$C_4$ alkoxy, halo (preferably chloro), trifluoromethyl, cyano or $C_1$-$C_4$ alkanesulphonamido, and $Z^1$ is O or $CH_2$.

The pharmaceutically acceptable salts of the compounds of formula (I) include acid addition salts such as the hydrochloride, hydrobromide, sulphate or bisulphate, phosphate or hydrogen phosphate, acetate, berylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol, and recovering the acid addition salt either as a precipitate, or by evaporation of the solution.

DETAILED DESCRIPTION OF THE INVENTION

The compounds of the formula (I) can be prepared by the following routes:

Route A

This involves the reaction of a benzodiazepinone of the formula (II) with an alkylating agent of the formula (III), as follows:

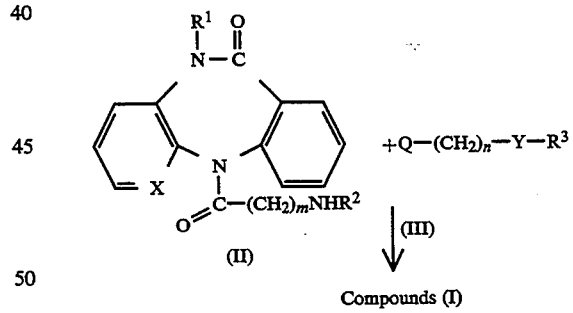

Compounds (I)

In the above, X, Y, $R^1$, $R^2$, $R^3$, m and n are as defined for formula (I) and Q is a leaving group, e.g. Br, Cl, $C_1$-$C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy. Most preferably, Q is Br.

The reaction is preferably carried out in the presence of an acid acceptor such as sodium hydrogen carbonate, sodium or potassium carbonate, triethylamine or pyridine, and in a suitable organic solvent, e.g. acetonitrile, at up to the reflux temperature. Reaction temperatures of 60°–120° C. are generally desirable and it is most convenient to carry out the reaction under reflux. Iodo is often a particularly suitable leaving group but since the starting materials (III) are sometimes most conveniently available as chlorides or bromides the reaction can also be carried out using the compound (III) as a chloride or bromide but in the presence of an iodide such as sodium or potassium iodide.

The starting materials of the formula (II) are either known compounds or can be prepared by conventional procedures, see e.g. J. Med. Chem., 1963, 6, 255, German Patentschrift no. 1,936,670, and British patent no. 1,581,500.

The starting materials of the formula (III) are again either known compounds or can be prepared conventionally: the preparation of any novel compounds of the formula (III) used in the Examples is in fact described in the following Preparations section.

Route B

This route can be represented schematically as follows:

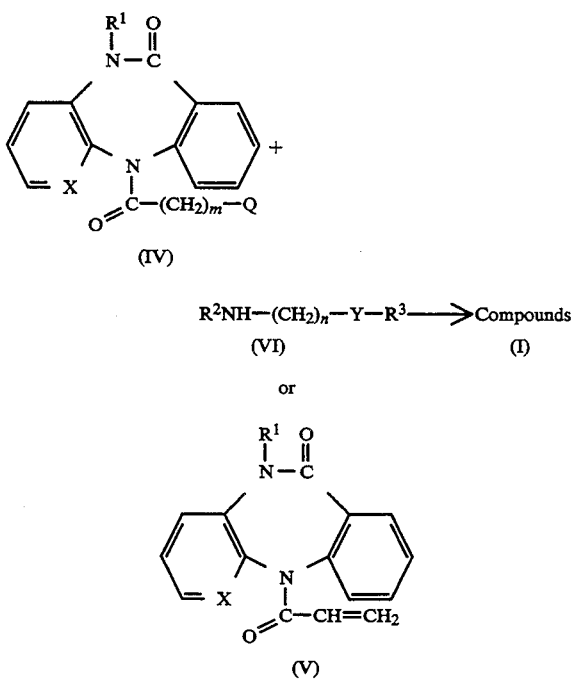

$R^1$, $R^2$, $R^3$, X, Y, m and n are as defined for formula (I) and Q is a leaving group such as is described in Route A. The reaction can be carried out similarly to Route A. Clearly use of the compound (V) will produce compounds (I) in which m is 2.

When m is 2, a mixture of the 11-(3-chloropropionyl) and 11-acryloyl compounds can be used: such a mixture is prepared in Preparation 1. Chromatographic techniques to separate the compounds can of course be used.

The compounds (IV) and (V) are either known (see e.g. GB 1,581,500 and DT-PS 1,936,670) or can be prepared by conventional techniques such as those described in the following Preparations 1 to 3.

The compounds (VI) are either known or can be prepared conventionally as is illustrated in the following Preparations.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency ef contraction of the spontaneously beating right atrium is derived from isometrically recorded contractions.

Dose-response curves to either acetylcholine (ileum) or carbachol (trachea, bladder and right atrium) are determined using a 1–5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration required to produce the original response is determined ($pA_2$ value - Arunlakshana and Schild (1959), Brit. J. Pharmacol., 14, 48–58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs of suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being with an effective amount of a compound of the formula (I), or a pharmaceutically acceptable salt or composition thereof.

The Examples illustrate the preparation of the compounds of the formula (I), and the Preparations illustrate the preparation of certain of the starting materials used in the preceding Examples.

EXAMPLE 1 5-{3-[N-(4-Methylphenethyl)-N-methylamino]propionyl}-10,11-dihydrodibenzo [b,e][1,4]diazepin-11-one

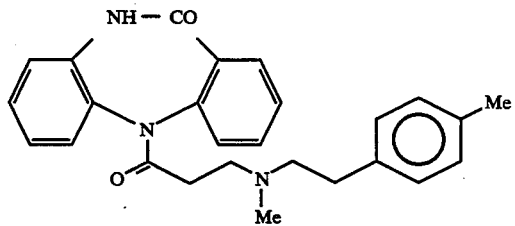

A mixture of 5-(3-methylaminopropionyl)-10,11-dihydrodibenzo [b,e][1,4]diazepin-11-one (0.20 g) (J. Med. Chem., 1963, 6, 255), 4-methylphenethyl bromide (0.14 g) and sodium hydrogen carbonate (60 mg) in acetonitrile (20 ml) was heated under reflux for 16 hours and evaporated. The residue was partitioned between water and dichloromethane and the organic layer washed with brine, dried over $MgSO_4$ and evaporated. The residue was purified by chromatography on silica using dichloromethane plus 0–20% methanol as eluant. Appropriate fractions were combined and evaporated and the residue crystallised from ether to give the title compound as a colourless solid, 60 mg (21%).

Analysis %: Found: C,75.1; H,6.5; N,10.0; $C_{26}H_{27}N_3O_2$ requires: C,75.5; H,6.6; N,10.2.

EXAMPLES 2-4

The following tabulated examples of the general formula:

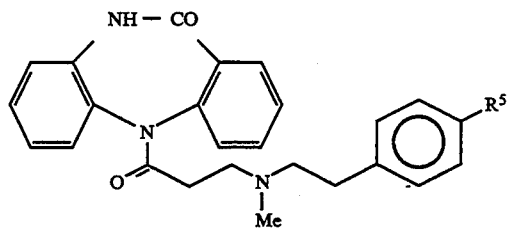

were prepared as described for Example 1 by reacting 5-(3-methylaminopropionyl)-10,11-dihydrodibenzo[b,e][1,4]-diazepin-11-one with a slight excess of the appropriate 2-arylethyl bromide in the presence of sodium hydrogen carbonate using acetonitrile as the solvent.

| Example | $R^5$ | Form characterised | Analysis % |
|---|---|---|---|
| 2 | —H | Colourless solid, m.p. 63–64° C. | Found: C,74.7; H,6.4; N,10.3; $C_{25}H_{25}N_3O_2$ requires C,75.2; H,6.3; N,10.5. |
| 3 | —Cl | Colourless solid, m.p. 68–70° C. | Found: C,69.5; H,5.8; N,9.4; $C_{25}H_{24}ClN_3O_2$ requires: C,69.2; H,5.6; N,9.7. |
| 4 | —OCH₃ | Colourless oil. | Found: C,72.5; H,6.5; N,10.1; $C_{26}H_{27}N_3O_3$ requires: C,72.7; H,6.3; N,9.8. |

EXAMPLE 5
5,11-Dihydro-11-{2-[N-(4-methoxyphenethyl)-N-methylamino]acetyl}-6H-pyrido[2,3-b][1,4]benzodiazepin-6-one

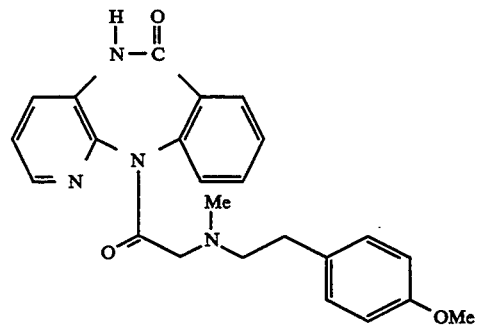

A mixture of 11-chloroacetyl-5,11-dihydro-6H-pyrido-[2,3-b][1,4]benzodiazepine-6-one (288 mg) (German patent 1,936,670), N-(4-methoxyphenethyl)methylamine (182 mg) and sodium hydrogen carbonate (92 mg) in acetonitrile (25 ml) was heated under reflux for 16 hours and evaporated. The residue was partitioned between 2M aqueous sodium hydrogen carbonate solution and dichloromethane and the organic layer washed with brine, dried over $MgSO_4$ and evaporated. The residue was purified by chromatography on silica using dichloromethane plus 0–10% methanol as eluant. Appropriate fractions were combined and evaporated and the residue crystallised from ethyl acetate to give the title compound as a colourless solid, 216 mg (52%).

Analysis %: Found: C,69.2; H,5.8; N,13.5; $C_{24}H_{24}N_4O_3$ requires: C,69.2; H,5.8; N,13.4.

EXAMPLES 6–10

The following tabulated Examples of the general formula:

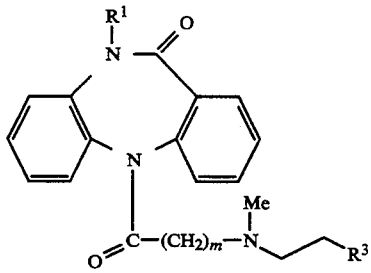

were prepared as described for Example 5 by reacting the appropriate 5-chloroacyl-10,11-dihydrodibenzo[b,e][1,4]diazepin6-one with one equivalent of the appropriate arylalkylmethylamine in the presence of two equivalents of sodium hydrogen carbonate using acetonitrile as the solvent. The product of Example 10 was characterised as containing 0.10 equivalents of dichloromethane (derived from the chromatography) while the product of Example 8 was characterised as a hydrate. The preparation of the starting material for Examples 6–8 is described in Preparation 2 while the preparation of the starting material for Example 9 is described in Preparation 3. The starting material for Example 10 was prepared according to German patent no. 1,936,670.

EXAMPLE 11

5,11-Dihydro-11-[3-[N-(4-methoxyphenethyl)-N-methylamino]-propionyl-6H-pyrido[%,3-b][1,4]benzodiazepin-6-one

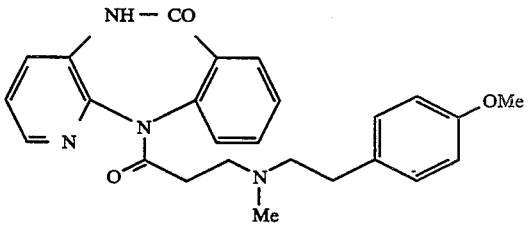

A mixture of 11-acryloyl-5,11-dihydro-6H-pyrido[2,3-b]-[1,4]benzodiazepin-6-one (185 mg) (see Preparation 1) and N-(4-methoxyphenethyl)methylamine (127 mg) in dioxane (15 ml) was heated under reflux for 4 hours and evaporated. The residue was partitioned between water and dichloromethane and the organic layer dried over MgSO$_4$ and evaporated. The residue was purified by chromatography on silica using dichloromethane plus 0–2% methanol as eluant. Appropriate fractions were combined and evaporated to give the title compound as a pale yellow solid, 182 mg (60%), m.p. 163°–164° C., which was characterised as a hemihydrate.

Analysis %:
Found: C,68.0; H,6.2; N,12.6;
$C_{25}H_{26}N_4O_3 \cdot 0.5\ H_2O$ requires: C,68.3; H,6.2; N,12.7.

EXAMPLES 12–21

The following tabulated Examples of the general formula:

| Example No. | R$^1$ | m | R$^3$ | Form characterised | Analysis % |
|---|---|---|---|---|---|
| 6 | H | 3 | 4-MeO-phenyl | Colourless gum | Characterised by $^1$H-N.M.R. (CDCl$_3$)δ=7.1–8.3(m, 8H); 7.13(d, J$^3$=8Hz, 2H); 6.83(d, J=8Hz, 2H); 3.81(s, 3H); 2.1–2.8 (m, 8H); 2.24(s, 3H); 1.65–1.95(m, 2H). |
| 7 | H | 3 | 4-Cl-phenyl | Colourless foam | Found: C, 69.7; H, 5.9; H, 9.4; Calculated for C$_{26}$H$_{26}$ClN$_3$O$_2$: C, 69.3; H, 5.8; N, 9.4. |
| 8 | H | 3 | benzofuranyl | Colourless oil; hydrate | Found: C, 71.2; H, 6.5; N, 9.1; Calculated for C$_{28}$H$_{29}$N$_3$O$_3$·H$_2$O: C, 71.0; H, 6.6; N, 8.8. |
| 9 | Me | 3 | 4-MeO-phenyl | Colourless oil | Found: C, 73.5; H, 7.2; N, 9.0; Calculated for C$_{28}$H$_{31}$N$_3$O$_3$: C, 73.5; H, 6.8; N, 9.2. |
| 10 | Me | 2 | 4-MeO-phenyl | Colourless oil containing 0.10 equivalents of dichloromethane | Found: C, 71.9; H, 6.6; N, 9.3; Calculated for C$_{27}$H$_{29}$N$_3$O$_3$·0.1 CH$_2$Cl$_2$: C, 72.0; H, 6.5; N, 9.3. | as solvent. The products of Examples 12, 13, 16, 18 and 19 were characterised as hemihydrates.

| Example No | R³ | Form characterised | Analysis % |
|---|---|---|---|
| 12 | 4-CN-phenyl | Colourless solid, m.p. 82–83° C., hemihydrate | Found: C, 69.8; H, 5.5; N, 14.9; $C_{25}H_{23}N_5O_2.0.5\ H_2O$ requires: C, 69.1; H, 5.6; N, 16.1. |
| 13 | 3,4-diCl-phenyl | Colourless solid, m.p. 170° C., hemihydrate | Found: C, 59.8; H, 4.6; N, 11.4; $C_{24}H_{22}Cl_2N_4O_2.0.5\ H_2O$ requires: C, 60.2; H, 4.8; N, 11.7. |
| 14 | 4-CHMe₂-phenyl | Colourless solid, m.p. 66° C. | Found: C, 73.4; H, 6.8; N, 12.7; $C_{27}H_{30}N_4O_2$ requires: C, 73.3; H, 6.8; N, 12.7. |
| 15 | 4-CF₃-phenyl | Colourless solid, m.p. 66–68° C. | Found: C, 64.2; H, 4.9; N, 12.0; $C_{25}H_{23}F_3N_4O_2$ requires: C, 64.1; H, 4.9; N, 12.0. |
| 16 | 3-OMe-4-Me-phenyl | Colourless solid, m.p. 70–72° C., hemihydrate | Found: C, 68.7; H, 6.3; N, 12.3; $C_{26}H_{28}N_4O_3.0.5\ H_2O$ requires: C, 68.7; H, 6.4; N, 12.3. |
| 17 | 2-naphthyl | Colourless solid, m.p. 168–170° C. | Found: C, 73.4; H, 5.8; N, 12.2; $C_{28}H_{26}N_4O_2$ requires: C, 73.2; H, 5.9; N, 12.2. |
| 18 | 3-Cl-phenyl | Colourless solid, m.p. 69–71° C., hemihydrate | Found: C, 65.4; H, 5.3; N, 12.8; $C_{24}H_{23}ClN_4O_2.0.5\ H_2O$ requires: C, 64.9; H, 5.4; N, 12.6. |
| 19 | 2,3-dihydrobenzofuran-5-yl | Colourless solid, m.p. 155–157° C., hemihydrate | Found: C, 69.5; H, 6.3; N, 12.3; $C_{26}H_{26}N_4O_3.0.5\ H_2O$ requires: C, 69.2; H, 6.0; N, 12.4. |
| 20 | 2-pyridyl | Colourless solid, m.p. 63–65° C. | Found: C, 68.9; H, 5.9; N, 17.4; $C_{23}H_{23}N_5O_2$ requires: C, 68.8; H, 5.8; N, 17.4. |
| 21 | 3-Me-phenyl | Colourless solid, m.p. 141–142° C. | Found: C, 72.5; H, 6.4; N, 13.4; $C_{25}H_{26}N_4O_2$ requires: C, 72.4; H, 6.3; N, 13.5. |

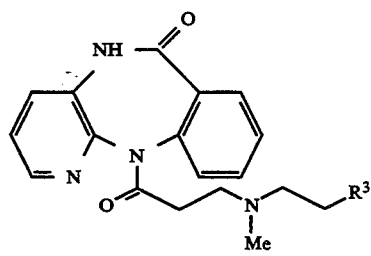

were prepared as described for Example 11 by reacting 11-acryloyl-5,11-dihydro-6H-pyrido[2,3-b][1,4]benzodiazepin-6-one (see Preparation 1) with a slight excess of the appropriate arylalkylmethylamine in the presence of excess sodium hydrogen carbonate using acetonitrile

EXAMPLES 22–30

The following tabulated Examples of the general formula:

| Example No. | Y | R³ | n | Form characterised | Analysis % |
|---|---|---|---|---|---|
| 22 | a direct link | 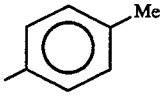 (phenyl with Me) | 2 | Colourless solid, m.p. 163–164° C. | Found: C, 72.1; H, 6.3; N, 13.7; $C_{25}H_{26}N_4O_2$ requires: C, 72.4; H, 6.3; N, 13.5. |
| 23 | a direct link | 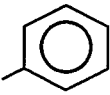 (phenyl) | 2 | Colourless solid, m.p. 144–145° C. hemihydrate | Found: C, 71.1; H, 6.3; N, 13.1; $C_{25}H_{26}N_4O_2 \cdot 0.5\ H_2O$ requires: C, 70.9; H, 6.4; N, 13.2. |
| 24 | a direct link | 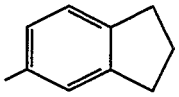 (indanyl) | 2 | Colourless solid, m.p. 171–172° C., hemihydrate | Found: C, 72.3; H, 6.5; N, 12.3; $C_{27}H_{28}N_4O_2 \cdot 0.5\ H_2O$ requires: C, 72.1; H, 6.5; N, 12.5. |
| 25 | O | 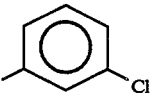 (phenyl with Cl) | 2 | Colourless solid, m.p. 67° C., hemihydrate | Found: C, 68.0; H, 5.9; N, 13.4; $C_{24}H_{24}N_4O_3 \cdot 0.5\ H_2O$ requires: C, 67.8; H, 5.9; N, 13.2. |
| 26 | a direct link | 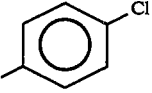 (phenyl with Cl) | 2 | Colourless solid, m.p. 150–151° C., hemihydrate | Found: C, 65.3; H, 5.2; N, 12.6; $C_{24}H_{23}ClN_4O_2 \cdot 0.5\ H_2O$ requires: C, 64.9; H, 5.4; N, 12.6. |
| 27 | a direct link | 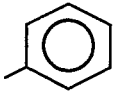 (phenyl) | 2 | Colourless solid, m.p. 144° C., hemihydrate | Found: C, 70.6; H, 6.0; N, 13.5; $C_{24}H_{24}N_4O_2 \cdot 0.5\ H_2O$ requires: C, 70.4; H, 6.1; N, 13.7. |
| 28 | a direct link | 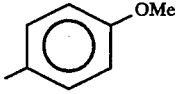 (phenyl with OMe) | 3 | Colourless solid, m.p. 48–50° C., hemihydrate | Found: C, 68.6; H, 6.1; N, 12.3; $C_{26}H_{28}N_4O_3 \cdot 0.5\ H_2O$ requires: C, 68.8; H, 6.4; N, 12.3. |
| 29 | O | 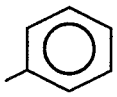 (phenyl) | 3 | Colourless solid, m.p. 65–67° C. | Found: C, 69.2; H, 6.1; N, 13.0; $C_{25}H_{26}N_4O_3$ requires: C, 69.7; H, 6.1; N, 13.0. |
| 30 | a direct link | 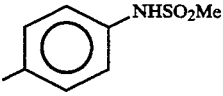 (phenyl with NHSO₂Me) | 2 | Colourless solid, m.p. 814–185° C. | Found: C, 60.7; H, 5.4; N, 14.1; $C_{25}H_{27}N_5O_4S$ requires: C, 60.8; H, 5.5; N, 14.2. |

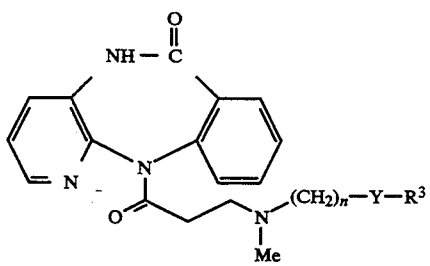

were prepared as described for Example 11 by reacting a mixture of 11-acryloyl-5,11-dihydro-6H-pyrido[2,3-b][1,4]benzodiazepin-6-one and 11-(3-chloropropionyl)-5,11-dihydro-6H-pyrido[2,B-b][1,4]- benzodiazepin-6-one (see Preparation 1) with a slight excess of the appropriate arylalkylmethylamine in the presence of excess sodium hydrogen carbonate using acetonitrile as solvent. The products of Examples 23–28 were characterised as hemihydrates. The N-(4-methanesulphonamidophenethyl)methylamine used in Example 30 was prepared as described in EP-A-245,997.

The following Preparations illustrate the preparation of certain of the starting materials used in the previous Examples.

Preparation 1
11-Acryloyl-5,11-dihydro-6H-pyrido[2,3-b][1,4]benzodiazepin-6-one and a mixture thereof with the corresponding 11-(3-chloro-propionyl) compound

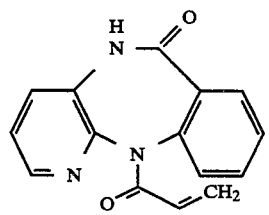

Solutions of 3-chloropropionyl chloride (6.3 g) in dioxane (60 ml) and triethylamine (8.4 g) in dioxane (60 ml) were added simultaneously to a refluxing suspension of 5,11-dihydro-6H-pyrido [2,3-b][1,4]benzodiazepin-6-one (9.45 g - see DT-PS 1179943) in dioxane (300 ml) and the mixture was heated under reflux for 6 hours and evaporated to give a mixture of the two title compounds in which the acryloyl compound predominated. Crude mixtures of the 11-acryloyl and 11-(3-chloropropionyl) compounds prepared using this procedure were used in Examples 22–30. The residue was purified by chromatography on silica using dichloromethane plus 0–2% methanol as eluant. Appropriate fractions were combined and evaporated to give the title 11-acryloyl compound as a colourless solid, 3.2 g, (27%) which was used directly in Examples 11–21.

Preparation 2 5-(4-Chlorobutyryl)-10,11-dihydrodibenzo[b,e][1,4]diazepin-11-one

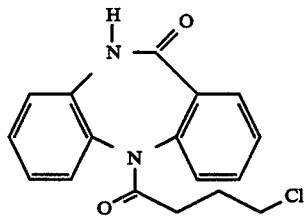

A mixture of 4-chlorobutyryl chloride (3.5 g) and 10,11-dihydrodibenzo[b,e][1,4]diazepin-11-one (4.2 g) (J. Med. Chem., 1963, 6, 767) in acetone (90 ml) was heated under reflux for 8 hours and evaporated. The residue was purified by chromatography on silica using hexane plus 0–100% dichloromethane as eluant. Appropriate fractions were combined and evaporated and the residue triturated with hexane/dichloromethane to give the title compound as a colourless solid, 1.62 g (26%), m.p. 151°–152° C.

Analysis %: Found: C,64.6; H,4.7; N,8.8; $C_{17}H_{15}ClN_2O_2$ requires: C,64.9; H,4.8; N,8.9.

Preparation 3
5-(4-Chlorobutyryl)-10,11-dihydro-10-methyldibenzo[b,e][1,4]-diazepin-11-one

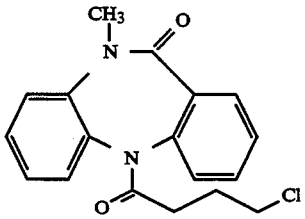

A mixture of 4-chlorobutyryl chloride (0.88 g) and 10,11-dihydro-10-methyldibenzo[b,e][1,4]diazepin-10-one (1.12 g) (J. Med. Chem., 1963, 6, 767) in acetone (25 ml) was heated under reflux for 4 hours and evaporated. The residue was dissolved in ethyl acetate and the solution washed with 10% aqueous sodium hydrogen carbonate solution, dried over $Na_2SO_4$ and evaporated. The residue was purified by chromatography on silica using hexane plus 0–100% dichloromethane as eluant. Appropriate fractions were combined and evaporated to give the title compound as a colourless oil, 1.10 g (67%).

Analysis %: Found: C,65.9; H,5.4; N,8.4; $C_{18}H_{17}ClN_2O_2$ requires: C,65.7; H,5.2; N,8.5.

Preparation 4 N-(3-Methylphenethyl)methylamine

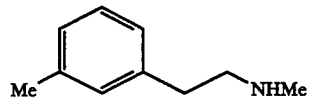

A mixture of 3-methylphenethyl bromide (2.22 g) and 33% ethanolic methylamine solution (30 ml) was heated in a bomb at 80° C. for 16 hours and evaporated. The residue was partitioned between water and dichloromethane and the organic layer dried over $MgSO_4$ and evaporated. The residue was purified by 421 chromatography on silica using dichloromethane plus 0–10% methanol as eluant. Appropriate fractions were combined and evaporated to give the title compound as a colourless oil, 0.44 g (27%), which was used directly in the preparation of Example 21 without characterisation.

Preparations 5–10

The following tabulated Preparations of the general formula:

were prepared as described for Preparation 4 by reacting the appropriate arylethyl bromide with 33% ethanolic methylamine solution. In each case the product was characterised by its $^1$H-N.M.R. spectrum. The preparation of the starting materials for Preparations 7, 10, 6 and 8 are described in Preparations 11, 12, 13 and 14. The product from Preparation 10 was obtained as a colourless solid.

| Preparation No. | $R^3$ | Form characterised | $^1$H-N.M.R. |
| --- | --- | --- | --- |
| 5 | ![CN-phenyl] | Yellow oil | $^1$H-N.M.R. (CDCl$_3$)δ=7.59(d, J=8Hz, 2H); 7.30(d, J$^3$=8Hz, 2H); 2.86(s, 4H); 2.63(s, 3H); 1.22(s, 1H). |

-continued

| Preparation No. | R³ | Form characterised | ¹H-N.M.R. |
|---|---|---|---|
| 6 | [4-CF₃-phenyl] | Yellow oil | ¹H-N.M.R. (CDCl₃)δ=7.58(d, J=8Hz, 2H); 7.36(d, J³=8Hz, 2H); 2.85(s, 4H); 2.44(s, 3H); 1.37(s, 1H). |
| 7 | [indanyl] | Dark oil | ¹H-N.M.R. (CDCl₃)δ=6.8–7.4(m, 3H); 2.60–3.05(m, 4H); 2.43(s, 3H); 2.05(t, J=7Hz, 2H); 1.90(s, 1H). |
| 8 | [2-OMe-5-Me-phenyl] | Yellow oil | ¹H-N.M.R. (CDCl₃)δ=6.97–7.08(m, 2H); 6.79(d, J=8Hz, 1H); 4.92(broad s, 1H); 3.81(s, 3H); 2.88–3.00(m, 4H); 2.57(s, 3H); 2.21(s, 3H). |
| 9 | [4-CHMe₂-phenyl] | Yellow oil | ¹H-N.M.R. (CDCl₃)δ=7.06–7.24(m, 4H); 2.80–3.00(m, 5H); 2.46(s, 3H); 2.06 (broad s, 1H); 1.24(d, J=7Hz, 6H). |
| 10 | [2,3-dihydrobenzofuranyl] | Colourless solid, m.p. 153–155° C. | ¹H-N.M.R. (CDCl₃)δ=7.11(s, 1H); 6.99 (d, J=8Hz, 1H); 6.77(d, J=8Hz, 1H); 4.58(t, J=7Hz, 2H); 3.13(s, 4H); 3.11 (t, J=7Hz, 2H); 1.13(broad s, 1H). |

Preparation 11  5-(2-Bromoethyl)indane

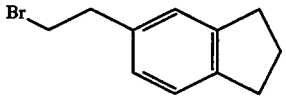

Phosphorus tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate solution. The layers were separated and the aqueous layer extracted wilth dichloromethane (2×100 ml). The combined dichloromethane extracts were dried (MgSO4) and concentrated in vacuo to give an oil which was purified by column chromatography on silica eluting with dichloromethane. The product-containing fractions were combined and concentrated in vacuo to give the title compound as a colourless oil, yield 10.5 g.

¹H N.M.R. (CDCl₃) δ=7.00–7.30 (m, 3H); 3.60 (m, 2H); 3.20 (m, 2H); 2.85–3.00 (m, 4H); 2.05–2.20 (m, 2H).

Preparation 12–14

The following tabulated Preparations of the general formula:

were prepared as described for Preparation 11 by reacting the appropriate arylethyl alcohol with phosphorus tribromide in carbon tetrachloride solution. In each case the product was obtained as a yellow oil which was characterised by its ¹H-N.M.R. spectrum. The preparation of the starting materials for Preparations 12 and are described in Preparations 15 and 16, respectively.

| Preparation No. | R³ | ¹H-N.M.R. (CDCl₃), δ |
|---|---|---|
| 12 | [2,3-dihydrobenzofuranyl] | 7.10(s, 1H); 6.95–7.00(d, 1H); 6.70–6.80(d, 1H); 4.60(t, J=7Hz, 2H); 3.55(t, J=7Hz, 2H); 3.20(t, J=7Hz, 2H); 3.12(t, J=7Hz, 2H). |
| 13 | [4-CF₃-phenyl] | 7.62(d, J=8Hz, 2H); 7.39(d, J=8Hz, 2H); 3.63(t, J=7Hz, 2H); 3.24(t, J=7Hz, 2H). |
| 14 | [2-OMe-5-Me-phenyl] | 7.01–7.07(m, 2H); 6.79(d, J=8Hz, 2H); 3.84(s, 3H); 3.58(t, J=7Hz, 2H); 3.10(t, J=7Hz, 2H); 2.22(s, 3H). |

Preparation 15  5-(2-Hydroxyethyl)-2,3-dihydrobenzofuran

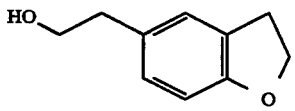

A solution of (2,3-dihydrobenzofuran-5-yl)acetic acid (4.9 g - see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide (1.5 ml) and, finally, water (4.5 ml). The mixture was filtered and the inorganic salts washed with ethyl acetate (2×50 ml). The filtrate and washings were combined and concentrated in vacuo to give the title compound as an oil, yield 3.3 g.

$^1$H N.M.R. (CDCl$_3$)δ–7.10 (s, 1H); 7.00 (d, J=8Hz, 1H); 6.75 (m, 1H); 4.55–4.65 (m, 2H); 3.75–3.90 (m, 2H); 3.15–3.30 (m, 2H); 2.80–2.90 (m, 2H); 1.75–1.85 (broad s, 1H).

Preparation 16  4-Trifluoromethylphenethyl alcohol

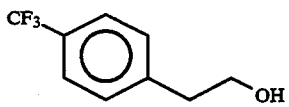

This was obtained by method described in Preparation 15 using 4-trifluoromethylphenylacetic acid instead of (2,3-dihydrobenzofuran-5-yl)acetic acid as the starting material. The title compound was obtained as a colourless oil, 3.75 g (80%), which was characterised by its $^1$H-N.M.R. spectrum.

$^1$H-N.M.R. (CDCl$_3$) δ=7.59 (d, J=8Hz, 2H); 7.38 (d, J=8Hz, 2H); 3.94 (t, J=7Hz, 2H); 2.97 (t, J=7Hz, 2H); 1.62 (s, 1H).

We claim:

1. A compound of the formula

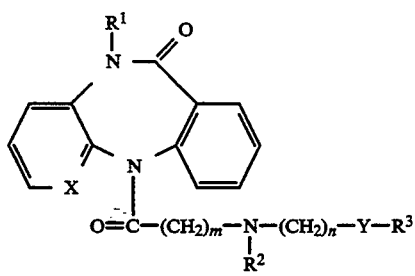

or a pharmaceutically acceptable salt thereof, wherein X is N or

where
R$^4$ is H, halo or C$_1$-C$_4$ alkyl;
R$^1$ is H or C$_1$-C$_4$ alkyl;
R$^2$ is H or C$_1$-C$_4$ alkyl;
Y is a direct link, O or S;
m is an integer of from 1 to 4;
n is 2 or 3; and R$^3$ is 1- or 2-naphthyl or a group of the formula:

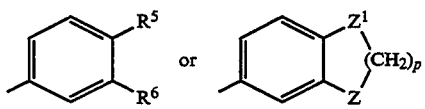

where
R$^5$ and R$^6$ are each independently H, C$_1$-C$_4$ alkyl, C$_1$-C$_4$ alkoxy, —(CH$_2$)$_q$OH, halo, trifluoromethyl, cyano, —(CH$_2$)$_q$NR$^7$R$^8$, —OCO(C$_1$-C$_4$ alkyl), —SO$_2$NH$_2$, —CONR$^9$R$^{10}$;
where either R$^7$ and R$^8$ are each independently H or C$_1$-C$_4$ alkyl, or
R$^7$ is H and R$^8$ is —SO$_2$(C$_1$-C$_4$ alkyl), —CONR$^9$R$^{10}$, —CO(C$_1$-C$_4$ alkyl) or —SO$_2$NH$_2$;
R$^9$ and R$^{10}$ are each independently H or C$_1$-C$_4$ alkyl;
q is 0, 1 or 2;
Z and Z$^1$ are each independently CH$_2$ or oxygen;
p is 1, 2 or 3;
with the proviso that when X is nitrogen, then YR$_3$ cannot be unsubstituted phenyl.

2. A compound as claimed in claim 1 wherein R$^1$ is H, X is N or CH, m is 1, 2 or 3, n is 2, R$^2$ is methyl and Y is a direct link or O.

3. A compound as claimed in claim 2 wherein R$^3$ is 2-naphthyl, or a group of the formula:

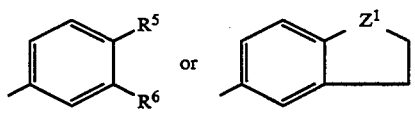

where R$^5$ and R$^6$ are each independently H, C$_1$-C$_4$ alkyl, C$_1$-C$_4$ alkoxy, halo, trifluoromethyl, cyano or C$_1$-C$_4$ alkanesulphonamido, and Z$^1$ is O or CH$_2$.

4. A pharmaceutical composition comprising a compound of the formula (I) as claimed in claim 1, or a pharmaceutically acceptable salt thereof, and a pharmaceutically acceptable diluent or carrier.

5. A method of treating irritable bowel syndrome in a patient in need of such treatment, characterised by administering to said patient an effective amount of a compound of the formula (I) or pharmaceutically acceptable salt thereof as claimed in claim.

6. A method of treating or preventing diseases associated with altered motility and/or tone of smooth muscle comprising administering to a patient a muscarinic receptor antagonist effective amount of a compound according to claim

* * * * *